United States Patent [19]

Billing

[11] Patent Number: 5,330,896

[45] Date of Patent: Jul. 19, 1994

[54] MONOCLONAL ANTIBODIES TO AN AUTOCRINE GROWTH FACTOR ANTIGEN THAT BINDS TO ACTIVATED LYMPHOCYTES AND CANCER CELLS

[76] Inventor: Ronald J. Billing, 9883 Pacific Heights Blvd.; Suite G, San Diego, Calif. 92121

[21] Appl. No.: 463,087

[22] Filed: Jan. 10, 1990

Related U.S. Application Data

[63] Continuation-in-part of Ser. No. 115,739, Oct. 8, 1987, abandoned, which is a continuation-in-part of Ser. No. 846,828, Mar. 31, 1986, abandoned, and a continuation of Ser. No. 469,608, Feb. 24, 1983, abandoned.

[51] Int. Cl.[5] .................. C07K 15/00; G01N 33/574
[52] U.S. Cl. .................... 435/7.23; 435/7.24; 435/7.8; 436/503; 436/518; 436/536; 436/813; 540/399; 530/403; 530/828
[58] Field of Search ............ 435/7.23, 7.24, 7.8; 436/503, 518, 536, 813; 514/2; 530/351, 397, 399, 828, 403; 424/85.8, 88, 9, 85.1

[56] References Cited

U.S. PATENT DOCUMENTS

| | | | |
|---|---|---|---|
| 4,613,459 | 9/1986 | Cantor et al. | 530/351 |
| 4,832,940 | 5/1989 | Ege | 424/1.1 |
| 5,017,691 | 5/1991 | Lee et al. | 530/351 |

OTHER PUBLICATIONS

L. Rimsky et al., *Jour. Immunol.*, 136, 3304–3310, 1986.
T. Kupper et al., *Chem. Abst.* 107 (13), 114014r, 1987.
Wakasugi et al., *Proc. Natl. Acad. Sci.* USA, 87, 8282–8286, 1990.

*Primary Examiner*—David Saunders
*Attorney, Agent, or Firm*—Klein & Szekeres

[57] ABSTRACT

A monoclonal antibody recognizing an autocrine growth factor that reacts with activated lymphocytes and cancer cells is described. The growth factor, a small glycoprotein is distinct from interleukin 2 and other known growth factors by function, structure and tissue distribution. A homologous growth factor is present in lymphoid tissues of a wide range of vertebrate species. Diagnostic and therapeutic uses of the growth factor and antibody-growth factor complex are disclosed. Also disclosed are therapeutic uses of synthetic analogues and peptide derivatives of the antigen.

3 Claims, 9 Drawing Sheets

MONOCLONAL ANTIBODIES TO AN AUTOCRINE GROWTH FACTOR ANTIGEN THAT BINDS TO ACTIVATED LYMPHOCYTES AND CANCER CELLS

BACKGROUND OF THE INVENTION

This is a continuation-in-part application of Ser. No. 07/115,739, filed Oct. 8, 1987, now abandoned, which is a CIP of 06/846,828, filed Mar. 31, 1986, now abandoned, and which is a continuation of 06/469,608, filed Feb. 24, 1983, now abandoned.

At the present time the general treatment of organ transplant rejection is accomplished with the use of medications such as azathioprine, prednisone and cyclosporine. The lack of specificity of these drugs produces side effects that limits their dose and effectiveness. In addition some treatments are expensive, and are required to be given for long durations. The invention overcomes these problems because of its specificity, lack of side effects and long term therapeutic effects. Clinical studies show that a single course of treatment will significantly improve the yearly survival rate of kidney grafts from unrelated donors which is now approximately 50%. It will reverse acute rejections that are resistant to currently available drug treatment. P. J. Morris (1985) Transplant Proceedings Vol XVII No 1 p 1153. The invention reverses immunological rejection which is still the main cause of transplant failure. It will help many patients who are unable to receive a transplant because of circulating antibodies directed against most donor tissues.

The invention is a monoclonal antibody (MA) and its antigen, which as a complex will effectively reverse acute organ transplant rejections without significant side effects. The use of a complex or growth factor of this specificity works by a mechanism of action that is different from previous approaches to organ rejection. This involves active immunotherapy by removing clones of antigraft lymphocytes. A short course of treatment produces several years of tolerance to the transplanted organ. The long term effect and specificity of action of the invention are significant advantages over current available antirejection therapies.

An additional property of the invention is that it can be used to enable those patients who need transplants but cannot be considered as recipients because of circulating antigraft preformed histocompatibility antibodies. The latter are eliminated by removal of specific clones of lymphocytes. There are no current treatments or therapies available to allow this large group of patients the option of receiving a transplant.

The MA described here was discovered by large scale screening of hybridoma cultures.

MAs are secreted from hybridomas made by fusing spleen cells from immunised normal mice and cancer cells called myelomas from the same species. The mice are immunised with cells that express the antigen that one desires a monoclonal antibody (MA) against. The subject MA was produced to a human leukemia cell line. Following the fusion hybridomas were selected by testing thousands of isolates for clones that secrete antibodies against desirable antigens. This is a lengthy and serendipitous method when cells are used as immunogens and requires extensive screening to produce the hybridoma clone described. The invention now allows similar hybridomas to be produced more easily by using purified antigen as the immunogen. An additional advantage of the invention is that the hybridoma cell line can be stored indefinitely in liquid nitrogen or grown in culture or ascites fluid to produce large quantities of reagent MA or growth factor.

The subject MA antibody-antigen complex has potential in the treatment of allergies and autoimmune diseases due to specific toxicity for immune cells that are actually causing the allergy or autoimmunity. These cells are a small percentage of lymphocytes called activated lymphocytes that are directed against specific allergens or antigens. The advantage of the invention over current treatments for these diseases is its increased effectiveness due to its unique mechanism of action against the cells causing the disease.

Non-specific reagents currently used are not as effective.

Cosimi et al (1981) New Engl J. Med 305 described a MA that reacts with a wide range of T lymphocytes. However its use in transplant rejection or autoimmune diseases is limited because it reacts with normal T cells required to combat infection. Most of the lymphocytes in the body are not involved in graft rejection and they are required for general immunity to pathogens. The invention overcomes this problem by its specificity for etiological agents of the disease, lymphocytes active against the transplanted tissue, allergens or autoantigens.

The invention is also useful for treatment of metastatic cancer.

Chemotherapy has improved survival rates in some cancers such as childhood leukemia but deaths from metastatic spread of solid tumors has not dramatically decreased in over 30 years.

The current invention overcomes the problem of metastasis not cured by conventional cancer treatments of chemotherapy, radiation and surgery. This is achieved again by its biological specificity for individual cell types and its ability to kill these cells without affecting healthy normal cells.

Clinical trials with tumor associated MAs have been described but thus far with limited success. (Cancer, Devita et al. 1985 Cancer, Lippincott Company, Philadelphia, p 133 and 2244). Although MA directed against cell membrane tumor antigens provide optimism for adjunctive cancer therapy the lack of specificity of available MAs has limited their effectiveness. The advantage of the current invention over prior art is in part due to its function as an essential growth factor. This enables it to be used to prevent the growth and division of certain cells causing disease.

Growth factor is a general term for molecules that stimulate and control the growth of cells mainly by binding initially to the cell membrane. Most cells in the body are in a slow growth or non dividing state. The majority of peripheral blood lymphocytes are not dividing unless they are activated by foreign antigens. Cancer cells are rapidly dividing cells of uncontrolled growth. Growth factors bind to receptors in cell membranes allowing nutrients to enter the cell and inducing a series of event that produce cell division. (Cancer, Devita et al. 1985, p 50 supra).

Cells growing in cultured nutrient medium require serum as a source of growth factors, (Gospodarowit D et al. Ann. Rev. Biochem. 451, 531 1976). Several of these serum growth factors have now been identified and purified; some are hormones such as insulin, erythropoietin and others are polypeptides that promote growth of certain normal tissue cells such as fibroblast growth factor, epidermal growth factor, nerve growth factor, platelet derived growth factor, transferrin. Interleukin 2 is a growth factor for activated normal T lymphocytes. Autotrine growth factors are produced by cancer cells themselves possibly from viral DNA integrated into the cell genetic material. They are shed into the cellular environment such as culture medium and cause further growth and cell division. (Cancer, Edited by V. T. Devita et al. 1985 p 50 supra).

MAs have been described that react to growth factor cell receptors but not to specific growth factors. For example the MA Tac reported by Uchiyama et al. J. Immunol. 1981, 126 1393-1397 appears to react with the interleukin 2 receptor on T cells. The following MAs appear to react with other growth factor receptors on activated cells: B3-25, described by Omary et al. (1980) Nature 286 888-891; 5E9, described by Haynes et al. (1981) J. Immunol. 127: 347-351; and OKT9, described by Reinherz et al. (1980) PNAS 77:10 1581-1592. All of the above react with the transferrin receptor of 180,000 daltons consisting of two equal protein chains of 90,000 daltons. 4F2 (Haynes et al. 1981 J. Immunol. 126, 1409-1414) reacts with an antigen of 120,000 daltons which is a heterodimer of 4OKD and 8OKD. The antigenic determinant, of the invention is itself a unique growth factor and not a receptor. The biological function, tissue distribution and properties distinguish the invention from other biological modifiers and prior art. It has the novel property of being able to inhibit the growth of dividing cells that cause disease or to stimulate immune cells that fight disease.

SUMMARY OF THE INVENTION

The present invention provides a monoclonal antibody and its antigenic determinant, an autocrine growth factor that stimulates the growth of cancer cells or lymphoblasts. The growth factor binds to a cell membrane receptor causing stimulation of cell growth. The growth factor alone and the complex of antibody and growth factor provide the main components of the invention that can be used to stimulate or inhibit cell growth. The MA alone will not bind to the cell membrane receptor unless it is bound to the antigen. The most effective form of the invention for treatment of transplant rejection is made by adding the growth factor to the MA to form a complex.

The unique structure of the antigen (see FIG. 10) allows an epitope to bind to the antibody whereas another identical epitope binds the antigen to the cell membrane receptor. By means of two identical but separate epitopes the antigen will bridge the antibody to the cell, it will link tumor cells together to form clumps and antibody molecules together to form precipitates. The MA complex does not react with the majority of normal tissue and blood cells. Similar bifunctional reagents to the invention described produce inter cell adherence such as that found in the early embryo genesis.

The nature and functions of the antigen determine the value and uniqueness of the MA and determine its medical uses. The determinant antigen is approximately 15,000 daltons and is located both on the cell membrane and in the cytoplasm of positive cells. The antigen has the properties of an autocrine growth factor. It is secreted into the culture media by cancer cells and stimulates the growth of cancer cells in general. By binding to the antigenic determinant, the MA will prevent the growth of the tumor cells in culture. The mechanism for this inhibition of growth appears to be that MA neutralises the antigenic determinant and thus inhibits its role of stimulating cell growth. When bound to the cell membrane receptor in the presence of complement, the MA complex causes cell lysis. In vivo, both active and passive immunotherapy occurs. Active immunity is produced by host humoral responses to the antigen.

The said growth factor from mouse, human, and other vertebrate sources is structurally homologous showing considerable crossreacativity between species.

The antigen is present in the cytoplasm of normal lymphoid cells and of activated lymphocytes and cancer cells. It can be isolated from these sources by cell lysis and purification by column chromatography, and affinity chromatography.

The invention provides immunotherapy for the treatment of cancer, reversal of transplant rejection, autoimmune diseases, allergies, and acquired immunodeficiency disease. The recipient of the transplanted organ reacts to the foreign graft by producing activated lymphocytes that attack the graft causing rejection of the transplanted organ. The antigen or antigen-MA complex will dramatically reverse transplant rejection without side effects to the patient. The therapeutic effect is long term suggesting that active immunotherapy is involved. The presence of circulating antibodies to the growth factor produced following injection of the antigen would support this mechanism. These antibodies lyse the activated lymphocytes responsible for the rejection whereas normal lymphocytes which are needed to protect the patient against infections are not lysed.

Phytohemaglutinin (PHA) activates lymphocytes and they are then reactive with the MA complex. PHA stimulation of lymphocytes in vitro is a model of what happens in the body during allergic reactions and autoimmune diseases. In these diseases activated lymphocytes are produced in response to a foreign allergen such as PHA. In the case of autoimmune diseases the body reacts to a molecule that is a functional part of the body itself. For example in rheumatoid arthritis the patient makes antibodies to his own immunoglobulin molecules, in multiple sclerosis there is an autoimmune reaction against parts of the nervous system and in systemic lupus antibodies are made against DNA. Activated lymphocytes are thought to be involved as an important mediator of the autoimmune disease process. Cell membrane binding tests have shown that circulating lymphocytes for patients with these diseases have a significant increase in numbers of MA positive (activated) cells, above normal control values. Removal of these activated cells by passive and active immunotherapy has therapeutic applications in patients with these disorders.

In passive therapy the MA antigen complex binds to the cell membrane receptor. Then serum complement components or other immune cells lyse the target cell. Normal cells have antigen in the cytoplasm but not on the cell surface and therefore are not reactive with the MA or growth factor.

The growth factor or MA antigen complex will induce active immunotherapy in the host by immunisation.

Immunization results in the production of a wide range of host induced antibodies against the growth factor. This represents a continual source of immunity against cancer cells and activated lymphocytes causing rejection with long term effect.

Other synthetic derivatives of the MA or antigenic growth factor may also be used as therapeutic agents. Synthetic peptides or antigenic derivatives can be therapeutic alone or coupled to cytotoxic agents such as chlorambucil (Ghose et al. (1975), Cancer 36:1646-1657), whole diphtheria toxin (Moolten et al. (1972) J. Natl. Cancer Inst. 49:1059-1062; Moolten et al. ibid 55:473-477; and Thorpe et al. (1978) Nature 271:752-755), and the A chain of ricin toxin (Oeltmann et al. (1979) J. Biol. Chem. 254:1022-1027; and Oeltmann et al., ibid, 254:1028-1032).

The subject antibodies and growth factor will also find use in the diagnosis of malignant and autoimmune diseases. The MA or antigen can be used to detect the presence of abnormal cells in tissue sections and diseases in which activated lymphocytes are present in the circulation.

Another aspect of the invention is immune enhancement provided by growth factor stimulation of lymphold cells. Purified antigen or synthetic derivations will boost the number of circulating lymphocytes. Other derivatives or analogues of the antigen can be made that block the cell membrane receptor and decrease cancer cells or pathogenic activated lymphocytes.

The growth factor can be used in serum free medium to stimulate the growth of cultured cells.

DEPOSIT OF HYBRIDOMA

The subject hybridoma was deposited on Feb. 24, 1983 at the ATCC, American Type Culture Collection, 12401 Parklawn Dr., Rockville, Md. 20852 and was given the ATCC number HB 8214.

BRIEF DESCRIPTION OF THE DRAWINGS AND TABLES

The file of this patent contains at least one drawing executed in color. Copies of this patent with color drawing(S) will be provided by the Patent and Trademark office upon request and payment of the necessary fee.

The following Figures and Tables will provide experimental results from which the characteristics of the MA and its antigen were determined. They will also give additional evidence of the uses of the invention described in the specification.

Table 1 shows the types of cells that react with the MA by cytotoxicity testing.

Table 2 gives the percentages of lymphocytes that express the antigenic determinant before and after stimulation with a mitogen PHA.

Table 3 shows growth study results with MA and antigenic determinant.

Table 4 shows allogeneic skin graft survival times in Rhesus monkeys treated with the MA complex and growth factor.

Figure 10:
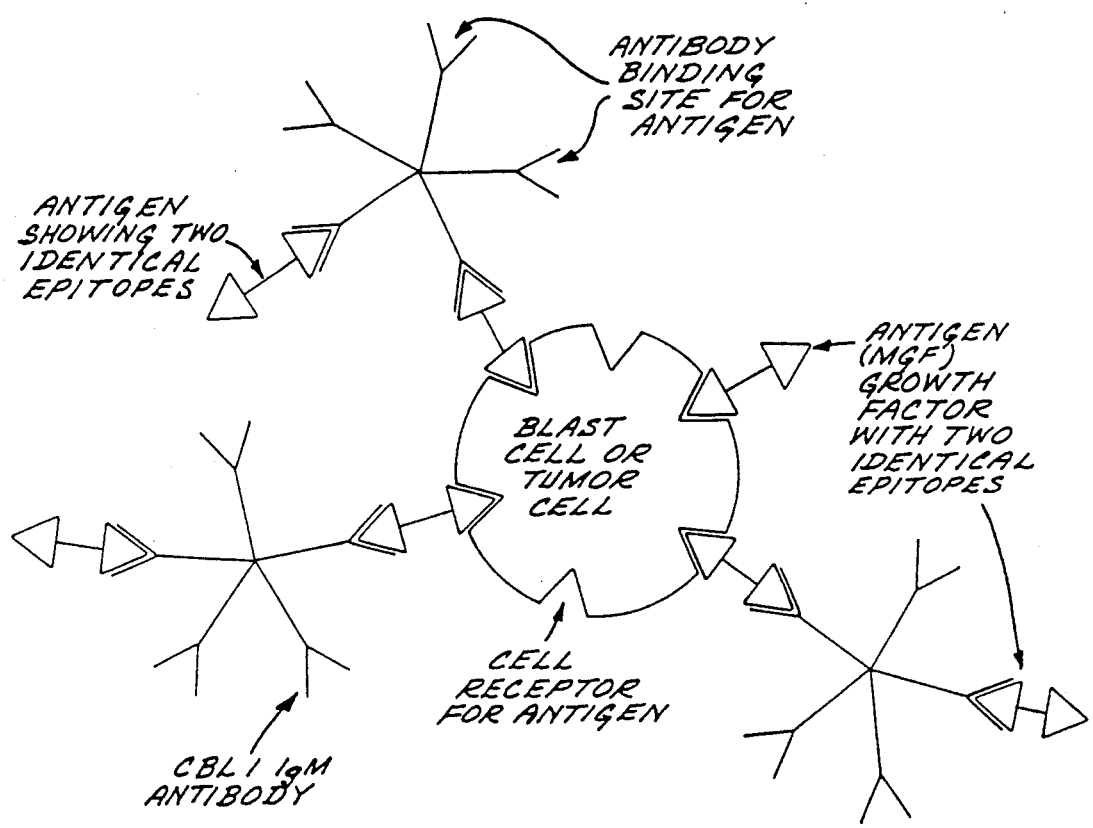
Figure 11:
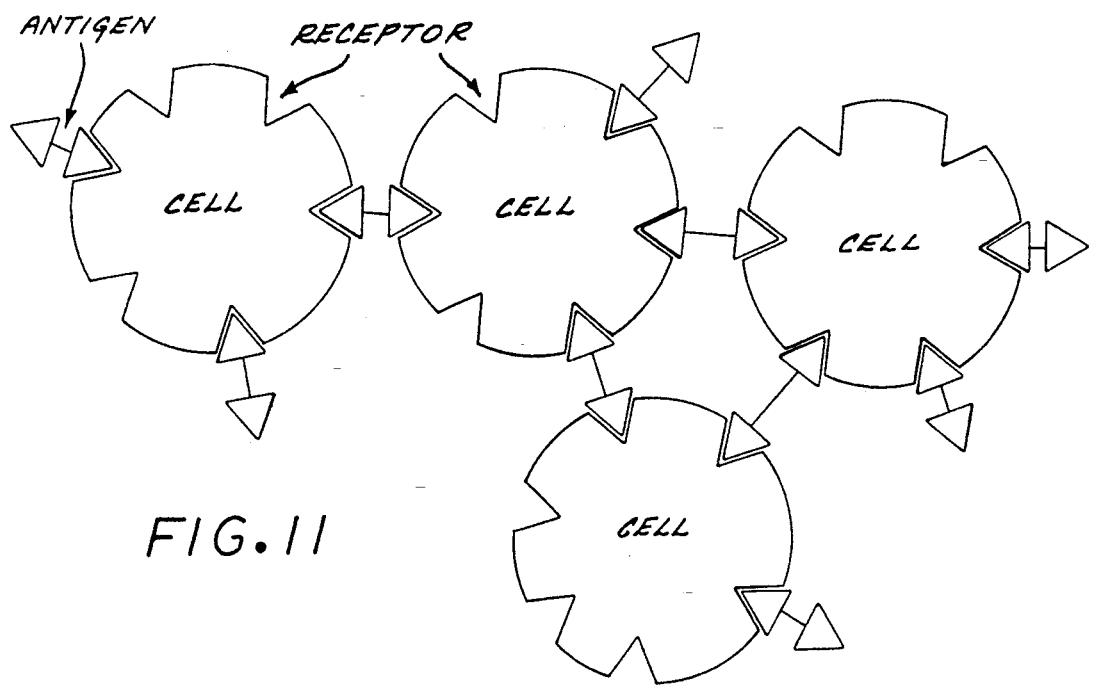
Figure 12:
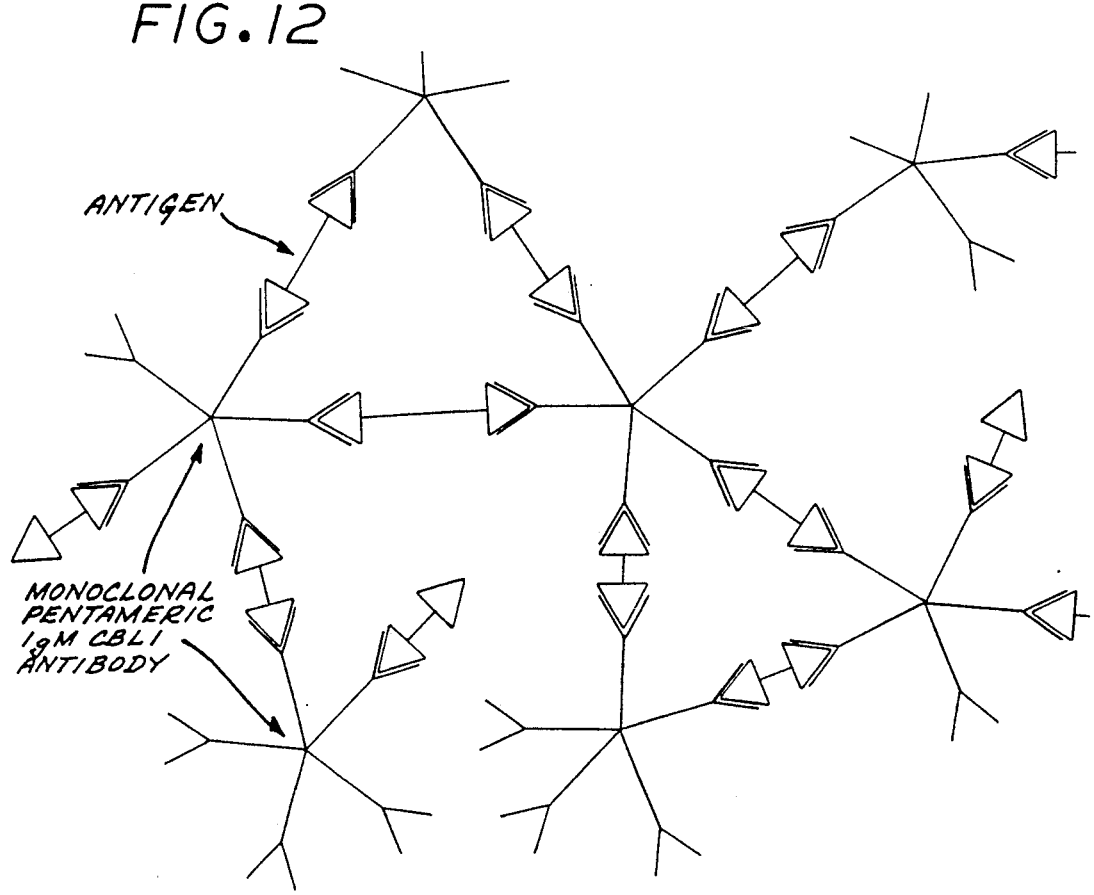

FIG. 10 and subfigures 10A, 10B and 10C, shows diagrammatic structure of MA and antigen complex and agglutination of cells.

DETAILED DESCRIPTION OF THE INVENTION

Method of Production of the Hybridoma and Monoclonal Antibody

Two 6 week old female Balb/c mice (Simonsen Labs) were immunised intravenously with $2 \times 10^6$ acute leukemia cells weekly for 3 weeks. Three days after the final injection the spleens were removed sterilely into RPMI medium and a single cell suspension of splenocytes made by teasing the tissue in RPMI medium with a scalpel. $2 \times 10^8$ spleen cells were fused with $50 \times 10^6$ P3×63 Ag8 651 myeloma cells (from ATCC) in 50% polyethylene glycol 4000 in RPMI medium. The fused cells were plated in six microtest plates containing 96 wells and allowed to grow in RPMI medium with 20% fetal calf serum containing hypoxanthine, aminopterin and thymidine. After three weeks, hybridoma colonies had grown out and supernatants from the microtest plate wells were screened by microcytotoxicity against the immunising cell and normal lymphocytes. One microtest plate from 600 produced a supernatant from a hybridoma that showed reactivity against tumor cells but not normal cells. This hybridoma was cloned by the limiting dilution method, expanded and frozen in liquid nitrogen. Other cloned cells were grown to produce ascites fluid in the peritoneal cavity of pristane primed Balb/c mice. $20 \times 10^6$ cells per mouse produced 4-6 ml ascitic fluid containing high levels of monoclonal antibody. The fusion and purification techniques are described in detail in Monoclonal Antibodies, 1980 ED by R. H. Kennet et al. Plenum Press, New York. The antibody was purified by ammonium sulfate (40%) precipitation followed by exclusion gel filtration on S300 (Sephadex ®).

The antigen can be purified from conditioned media and NP40 cell lysates by affinity chromatography using purified antibody bound to Sepharose or latex beads (Affinity chromatography by Pharmacia). Following washing of the column with phosphate buffered saline the antigen can be eluted by chaotropic agents or glycine buffer pH 2.8. This is neutralized by phosphate buffer and used alone or added to the purified antibody to make an active complex. It can also be purified by gel filtration, ion exchange chromatography, or lectin chromatography.

Materials Used in Characterisation of the MA

Leukemia cells: Heparinised peripheral blood samples were drawn from children and adults with active leukemia. The acute lymphocytic leukemia (ALL) and acute myelocytic leukemia (AML) patients had peripheral blood blast counts greater than 90%. Leukemia cells from patients and peripheral blood lymphocytes from healthy donors were isolated by Ficoll-Hypaque ® density gradient centrifugation. Leukemia cells were stored in liquid nitrogen.

Cell lines were grown in suspension cultures in RPMI 1640 containing 10% heat-inactivated fetal calf serum. Most were obtained from ATCC, Rockville, Md.

T and B lymphocytes: T and B lymphocytes were prepared from whole lymphocytes by the nylon-wool method. Danilovs et al. (1980) Histocompatibility Testing 1980, Terasaki (ed.) UCLA Tissue Typing Laboratory, Los Angeles, Calif., pp. 287-288.

PHA Blasts: Whole peripheral blood lymphocytes isolated by the Ficoll-Hypaque ® technique were cultured at 2.5×10⁶ in media (M199) with 20% human AB serum (heat inactivated) at 37° C. with 50ug/ml of Difco PHA under sterile conditions for 3-6 days. Control lymphocytes were incubated in M199 with 20% human AB serum without PHA. At the end of the culture period, cells were removed, washed and tested by microcytotoxicity against the blast sera.

Monocytes: Monocytes were isolated using a Percoll® density gradient. Gutierrez et al. (1979) Immunol. Meth. 29: 57-63. Briefly, the thrombin pellet from lymphocyte isolation containing monocytes, platelets, and granulocytes was washed and resuspended in 65% Percoll® in PBS (by volume). Then 55% Percoll®, 40% Percoll® and McCoy's media were layered, respectively, over the suspension and centrifuged at 3200×g for 10 min with the brake off. The monocytes were recovered from the 40-55% Percoll® interface, diluted with media and washed.

Granulocytes: Granulocytes were isolated from Ficoll® pellets by removing RBCs by agglutination. The Ficoll® pellet from lymphocyte isolation containing granulocytes and RBCs was suspended in McCoy's media and centrifuged at 3000×g for 1 min and the buffy coat from the pellet removed. This process was repeated until the buffy coat was sufficiently enriched for granulocytes. The appropriate agglutinin (anti-A, -B, -AB, -O, and -H) was added and allowed to agglutinate fully. The clumps were then spun at 1500×g for less than 1 sec and the supernatant layered over Ficoll® (1.3545 g/ml) and centrifuged at 3000×g for 2 min. The granulocyte-enriched pellet was then washed and tested against antiblast (This entire process was done in Fisher tubes using a Fisher, Model 59, centrifuge.).

Methods Used to Characterise CBL1 Reactivity

Cytotoxicity. Cytotoxicity tests measure the extent of killing of a cell population by cytotoxic monoclonal antibodies. The antibody binds to the cell surface and the cell is lysed or killed by complement components in serum. A dye and a microscope are used to count dead cells. Cytotoxicity is a natural method used by the body to kill tumor cells reactive with infused monoclonal antibodies. A rapid cytotoxic screening test was used to determine the specificity of the subject antibody for tumor cells and not normal cells. One microliter of antibody at dilutions from 1:10 to 1:10⁷ were added to 2000 viable cells in wells of a microtiter plate. Following incubation of 30 mins that allows the antibody time to bind to the cell, rabbit serum (5ul) was added for one hour. The complement components in the rabbit serum killed cells that bound antibody but not cells that did not bind antibody. The dead cells are identified by adding a red colored dye (eosin) which enters dead cells but not living cells. The number of dead cells can be counted using a light microscope at 200×magnification. (Billing et al 1979 Immunol. Immunopathol. 13, 435).

Tissue Staining. A different method of antibody binding test was used to identify the positive cells in tissue sections from patients. A thin slice (6-8 microns) of the frozen organ tissues was cut by a cryostat and placed on microscope slide. The tissue sections were fixed in acetone for 10 mins. Dilutions of the monoclonal antibody from 1:10 to 1:10,000 were added to the slides. They were incubated for 15 mins with a second antibody, peroxidase linked goat anti-mouse immunoglobulin. Following a wash step the substrate for the peroxidase enzyme, aminoethyl carbazole (AEC), was added for 10 mins. After a final wash the tissues were counterstained with Mayer's hematoxylin and preserved in aquamount (Lerner Laboratories). The cells that contained the antigen stained a reddish brown color whereas negative cells and tissue stained pale blue due to the counterstain, Mayer hematoxylin. Control studies included staining with normal mouse ascites and a mouse monoclonal antibody against normal human leukocytes.

Molecular weight of the antigenic determinant. The method of Immuno-precipitation and Polyacrylamide Gel Electrophoresis was used. Cells (5×10⁶ per experiment) were labelled with $^{25}$I by the iodogen technique of Markwell and Fox (1978) Biochemistry 17: 4807-4817, solubilised with 300 ml 0.5% Nonidet® P40, and immunoprecipitated with 10ul of the MA bound to 40ul rabbit anti-mouse IgM-protein A Sepharose 4B. After washing three times with PBS, the precipitated antigens were released from the protein A by adding 50ul 2% SDS. They were boiled for 2 mins with or without dithiothreitol and run on 12% gels. Fifty 2 mm slices from each gel were counted on a gamma counter. Standard proteins of known molecular weight were also run in order to calculate the molecular weight of the precipitated antigens. The gel system was that originally described by King and Laemmli (1971) J. Mol. Biol. 62: 467-480, and used by Billing et al. (1978) J. Natl. Cancer Inst. 61: 423-429. The molecular weight and protein standards used were lysozyme 14,400, soybean trypsin inhibitor 21,500, carbonic anhydrase 31,000, ovalbumin 45,000, bovine serum albumin 68,000, phosphorylase B 92,900, and B-galactosidase 116,500. The extreme mobility and negative charge of the antigen made slab gel electrophoresis followed by western blot analysis difficult.

The molecular weight of the antigen detected by the subject antibody was estimated from a graph of the migration distances of the standards plotted against their molecular weight. Tumor cells or spent culture media were used as a source of the antigen.

SDS electrophoresis of the monoclonal antibody and immunodiffusion studies with antimouse immunoglobulin subtype antisera demonstrated that the monoclonal antibody was of the IgM subclass.

TABLE I

MONOCLONAL ANTIBODY REACTIONS AGAINST NORMAL AD MALIGNANT CELLS

| | # samples | % positive |
|---|---|---|
| Normal cells - Type | | |
| Peripheral blood T cells | 12 | <2% |
| Peripheral blood B cells | 12 | <2% |
| Peripheral blood granulocytes | 12 | <2% |
| Peripheral blood platelets | 10 | <2% |
| Peripheral blood monocytes | 15 | >80% |
| Peripheral blood activated lymphocytes | 6 | >60% |
| Malignant cells - Type | | |
| Acute myeloid leukemias | 25 | >95% |
| Acute lymphoid leukemias | 28 | >95% |
| Chronic myeloid blast crisis | 10 | >95% |
| Chronic lymphocytic leukemias | 20 | <2% |
| Cultured leukemia cell lines, Reh, CEM, HSB2, Daudi, Raji, HL60, KG, JM, Molt 4, BJAB | 10 | >95% |
| Tumor cell lines | 16 | >95% |
| ( ) is the number of different cell lines tested: colorectal (3), lung (4), liver (1), breast (2), prostate (1), kidney (1), esophagus (2), bladder (2) | | |
| Tumor cells in frozen tissue sections | 20 | +ve by immunoperoxidase staining |

TABLE I-continued

MONOCLONAL ANTIBODY REACTIONS AGAINST NORMAL AD MALIGNANT CELLS samples   % positive ( ) is number of different carcinomas tested:
colon (6), rectal (1), esophageal (2), breast (5)
kidney (1), meningioma (3), pancreatic (1), adrenal (1).

A. Characterisation of the MA Reactivity

Table 1 shows the results of testing the MA for killing of human cell types. The cells that were highly positive were cultured solid tumor cells, leukemia cells, activated lymphocytes and monocytes. Most normal non-dividing tissue cells were not reactive. Therefore the invention antibody is reactive with an antigen that is present essentially on cells that are dividing. Activated lymphocytes are dividing under normal immunological conditions in that they have been stimulated to divide as part of the normal immune response to a foreign antigen. Cancer cells are dividing uncontrollably.

The photographs (FIG. 1-4) show tissue sections of colon and breast cancer tissue stained with the MA and goat anti-mouse immunoglobulin bound to peroxidase. The substrate is aminoethyl carbazole (AEC) which gives a positive reddish-brown stain. The tissues are counter-stained with Mayer hematoxylin which shows a background intensity of blue proportional to the cell density. The photographs demonstrate the specificity of the MA for tumor tissue.

Figure 1:
FIG. 1-4 shows photographs of staining of tissue sections with the MA complex.

FIG. 1 shows colon carcinoma stained with the MA. Magnification is 250×. The malignant tissue that is present on the left side of the photograph is stained reddish-brown showing reaction with the MA, whereas the normal colon endothelium on the right is negative. The large blue mass at the top right of center is a lymph node showing no reaction with the MA.

Figure 2:
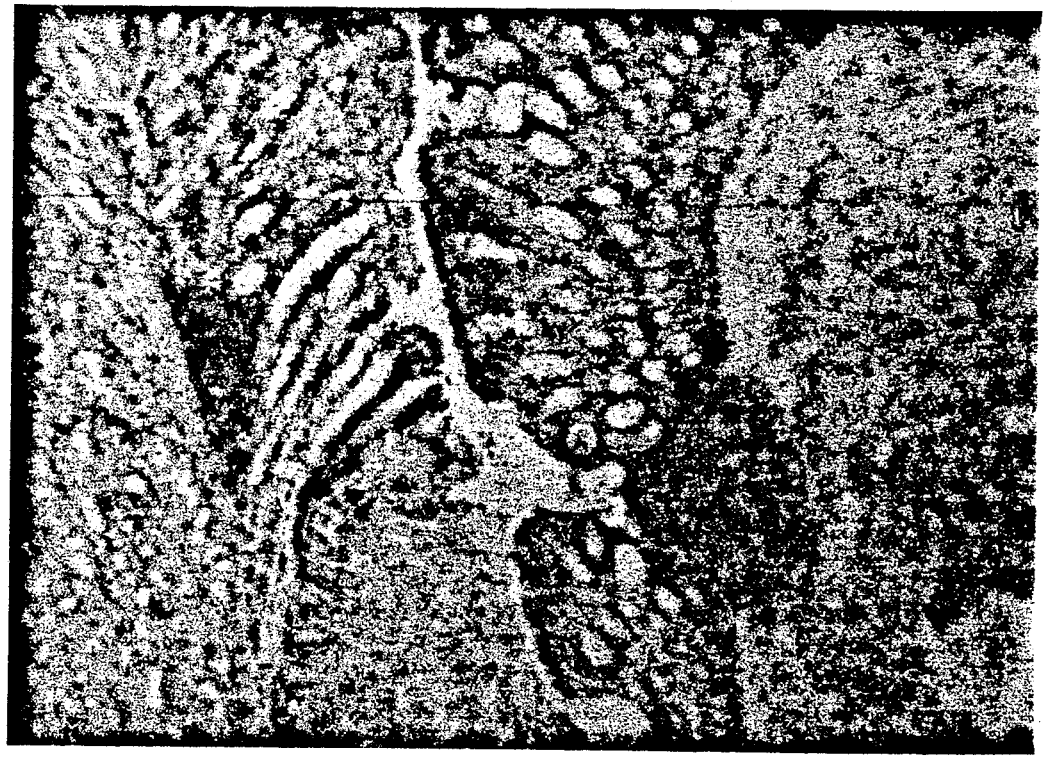

FIG. 2 shows the same colon carcinoma section stained with mouse monoclonal antibody against normal or human lymphocyte antigen (T29). Magnification 250×. This is a negative control for the subject MA. T29 does not stain the tumor tissue on the left but stains lymphoid cell infiltrates in the endothelium on the right and the normal lymph node (lower right).

Figure 3:

FIG. 3 shows breast cancer tissue stained with the MA. Magnification 100×. The malignant cells surrounding the glandular ducts are positive whereas the normal stroma is negative.

Figure 4:
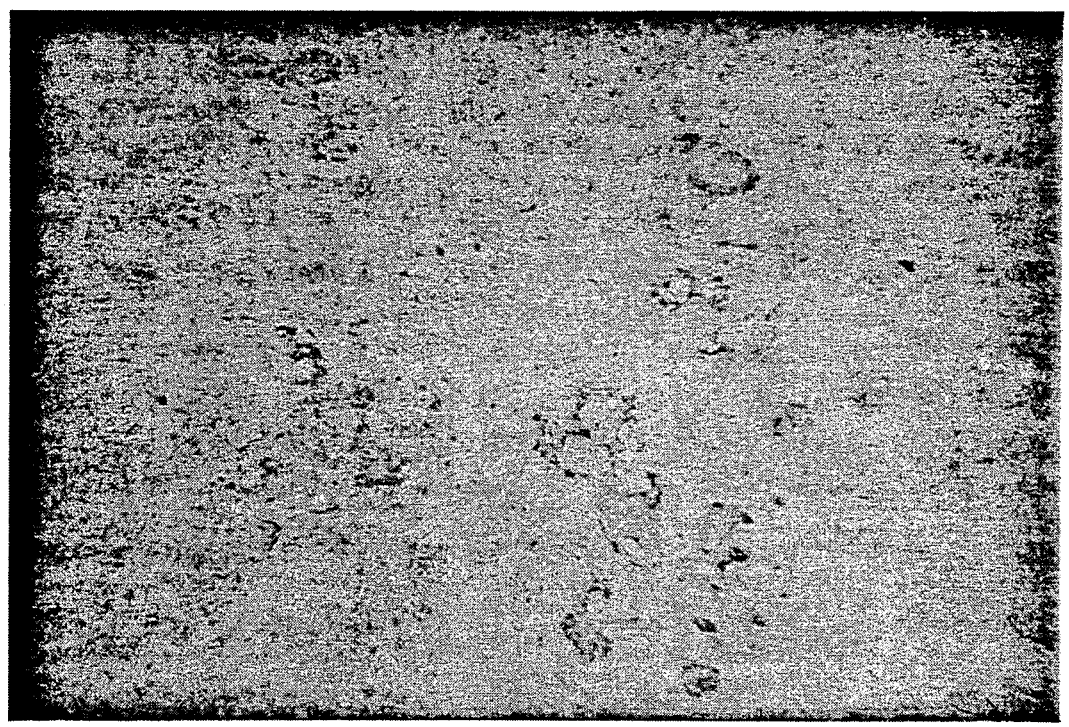

FIG. 4 shows normal breast tissue stained with the MA. Magnification 100×. There are no stained cells.

In addition to the tissues shown in the photographs, the following different carcinomas were stained positive with the subject MA. The number in parenthesis represents the number of patients tested:- colon (6), rectal (1), esophageal (2), breast (5), kidney (1), meningioma (3), pancreatic (1), adrenal (1). Normal tissue from healthy donors and normal tissue adjacent to malignant tissue was not stained and therefore unreactive with the MA.

B. Presence of antigenic determinant on activated lymphocytes.

Table 2 illustrates by immunoperoxidase staining of lymphocytes with the antibody that the antigen is present in the cytoplasm of unstimulated normal lymphocytes. It is not present on the cell surface of these cells. Five hours following stimulation of the lymphocytes with PHA or allogeneic lymphocytes, the antigen is present on the cell surface membrane in addition to also being in the cytoplasm. Therefore the antigen must have some function at the cell membrane of activated or dividing cells. This function as described below appears to be that of a growth promoting agent or growth factor. As a control, the OKT9 antibody that reacts with blast cells was present only on the surface of activated cells. The antigen is unique in that it is found in the cytoplasm but not the cell surface of non-dividing lymphocytes and it is present on the cell surface of dividing cells such as activated lymphocytes and cancer cells.

TABLE 2

PERCENT POSITIVE CELLS IN CULTURE OF PHA STIMULATED VERSUS UNSTIMULATED PERIPHERAL BLOOD LYMPHOCYTES

| STAINING ANTIBODY | PERCENTAGE CELLS WITH POSITIVE SURFACE STAINING | | PERCENTAGE CELLS WITH POSITIVE CYTOPLASMIC | |
|---|---|---|---|---|
| | PHA | NO PHA | PHA | NO PHA |
| A. CBL1 (a)* | 44 | 0 | 97 | 97 |
| CBL1 (b) | 21 | 11 | 97 | 96 |
| CBL1 (c) | 20 | 3 | 91 | 92 |
| B. OKT9 (c) | 22 | 3 | 33 | <1 |
| OKT9 (d) | n.d. | n.d. | 30 | 5 |

*Lower case letters identify the individual PBL donors.

C. Growth Factor Studies

The antibody inhibits the division of tumor cells growing in tissue culture by binding to a soluble antigen in the culture medium (Table 3).

Serum free conditioned media supernatant from growing tumor cells at a density of $1 \times 10^6$/ml will support the growth of live tumor cells growing at a low density ($10^5$/ml). Without 20% conditioned media supernatant these tumor cell lines will die. They appear to need a growth factor which is present in the conditioned media. This growth factor could be blocked by the addition of 10-50 micrograms/ml of pure antibody but not by three other mouse monoclonal antibodies against lymphoid cell lines. The conditioned media growth factor could be removed and isolated from the conditioned media with MA affinity coated protein A beads as described on pages 15 and 16. The conditioned media growth factor and the cell surface antigen detected by the monoclonal antibody have the same molecular weight of approximately 15,000 daltons. This cancer cell related growth factor appears to be an autocrine factor meaning that it is produced and secreted by the tumor cells themselves into the cell media and stimulates growth of other cancer cells. It can be purified from growth media by ammonium sulfate precipitation followed by gel chromatography on G50 Sephadex ®. Treatment of the antigen with proteolytic enzymes will destroy its activity. A similar growth factor is present in mouse ascitic fluid and it may be associated with vertebrate cancers in general.

TABLE 3

RATES OF GROWTH OF TUMOR CELLS IN SERUM FREE CULTURE MEDIA IN THE PRESENCE OF GROWTH FACTOR AND MA

| ADDITIONS TO GROWTH MEDIUM | RATE OF GROWTH[1] |
|---|---|
| None | 0 |
| 20% Growth Medium (GM)[2] | + |
| 20% GM + CBL1[3] | 0 |
| 20% GM + B5[4] | + |
| Tumor cell lysate (TCL)[5] | + |
| TCL + CBL1 | 0 |

TABLE 3-continued
RATES OF GROWTH OF TUMOR CELLS IN SERUM FREE CULTURE MEDIA IN THE PRESENCE OF GROWTH FACTOR AND MA

| ADDITIONS TO GROWTH MEDIUM | RATE OF GROWTH[1] |
| --- | --- |
| TCL + B5 | + |
| Purified CAGF[6] | + |
| Purified CAGF + CBL1 | − |

[1] 0 = no growth, + = cell density increases 2 fold each day (average)
[2] Percentage of supernatant added from cells in log phase growth in serum free medium
[3] 50 ug purified MA
[4] Control MA
[5] 10 × 10[6] tumor cells lysed in 1 ml PBS by rapid freezing ad thawing followed by centrifugation
[6] Purified by ammonium sulfate precipitation and gel filtration

D. Animal Studies

Studies in animal models have shown that the MA is capable of prolonging skin allograft survival in Rhesus monkeys without an adverse side effect. Monkeys were 5-6 Kg and received up to 0.45 ml (5 mg) daily for 16 to 22 days. The six monkeys treated had no side effects and had significant prolonged skin graft (size 4×4 cm on forearm) survival durations of 20 days over that of four untreated controls in which skin grafts survived 5 days. Differential blood counts taken every other day revealed no changes and all animals were healthy and well. Results are shown in Table 4.

TABLE 4
SKIN GRAFT SURVIVAL IN RHESUS MONKEYS TREATED WITH MONOCLONAL ANTIBODY CBL1

| EXP # | ANIMAL # | TITER | DOSE/LAMDA | SKIN GRAFT SURVIVAL |
| --- | --- | --- | --- | --- |
| 1 | 17182 | $10^4$ | 300 | 16 days |
| 2 | 17083 | $10^4$ | 300 | 16 days |
| 3 | 17085 | $10^4$ | 300 | 15 days |
| 4 | 7633 | $10^4$ | 450 | 22 days |
| 5 | 7212 | $10^4$ | 450 | 20 days |
| 6 | 7253 | $10^4$ | 450 | 20 days |

E. Human Clinical Studies

Figure 5:
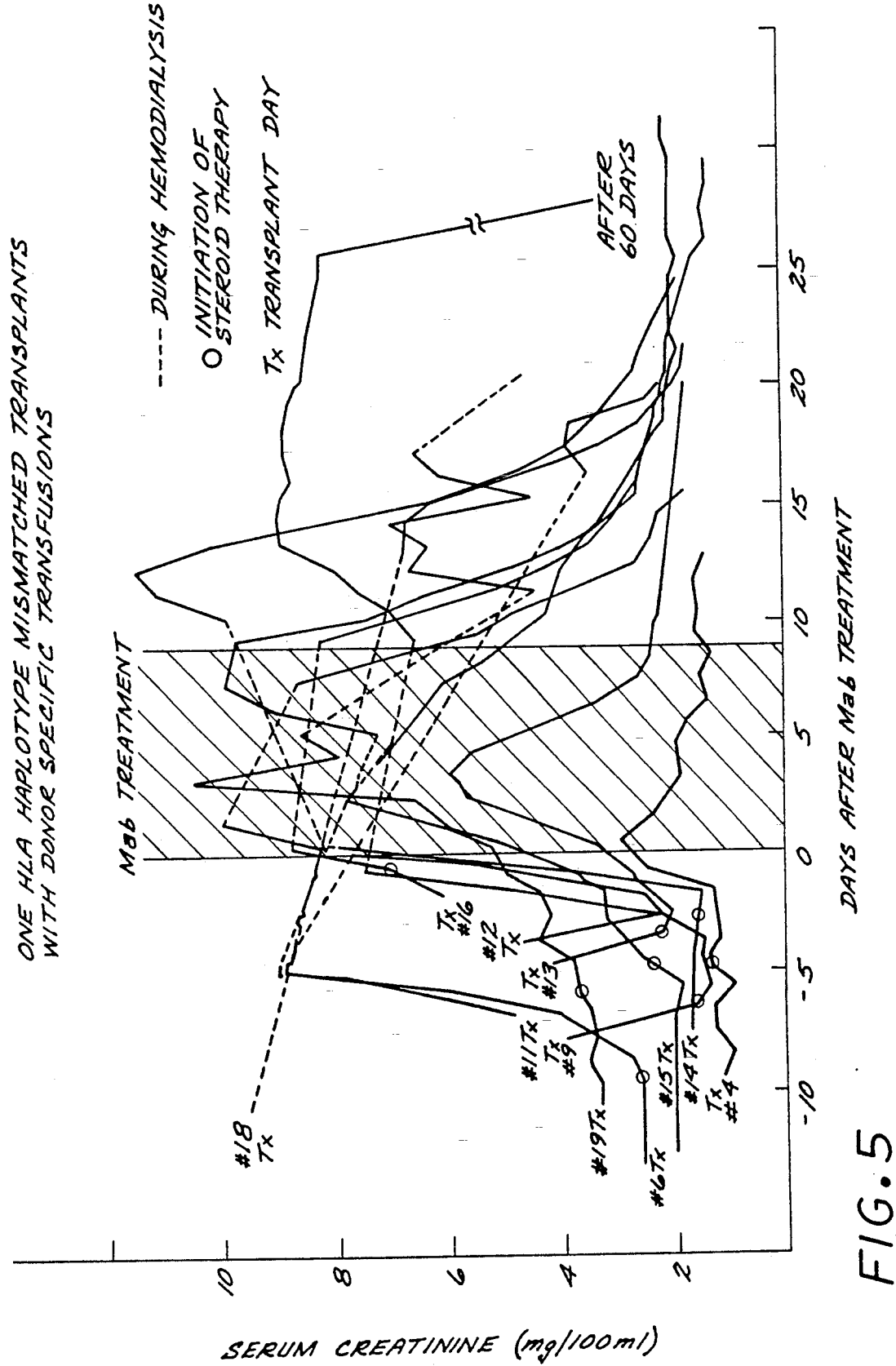
FIG. 5-7 shows rejection course monitored by serum creatinine of kidney transplants.
Figure 6:
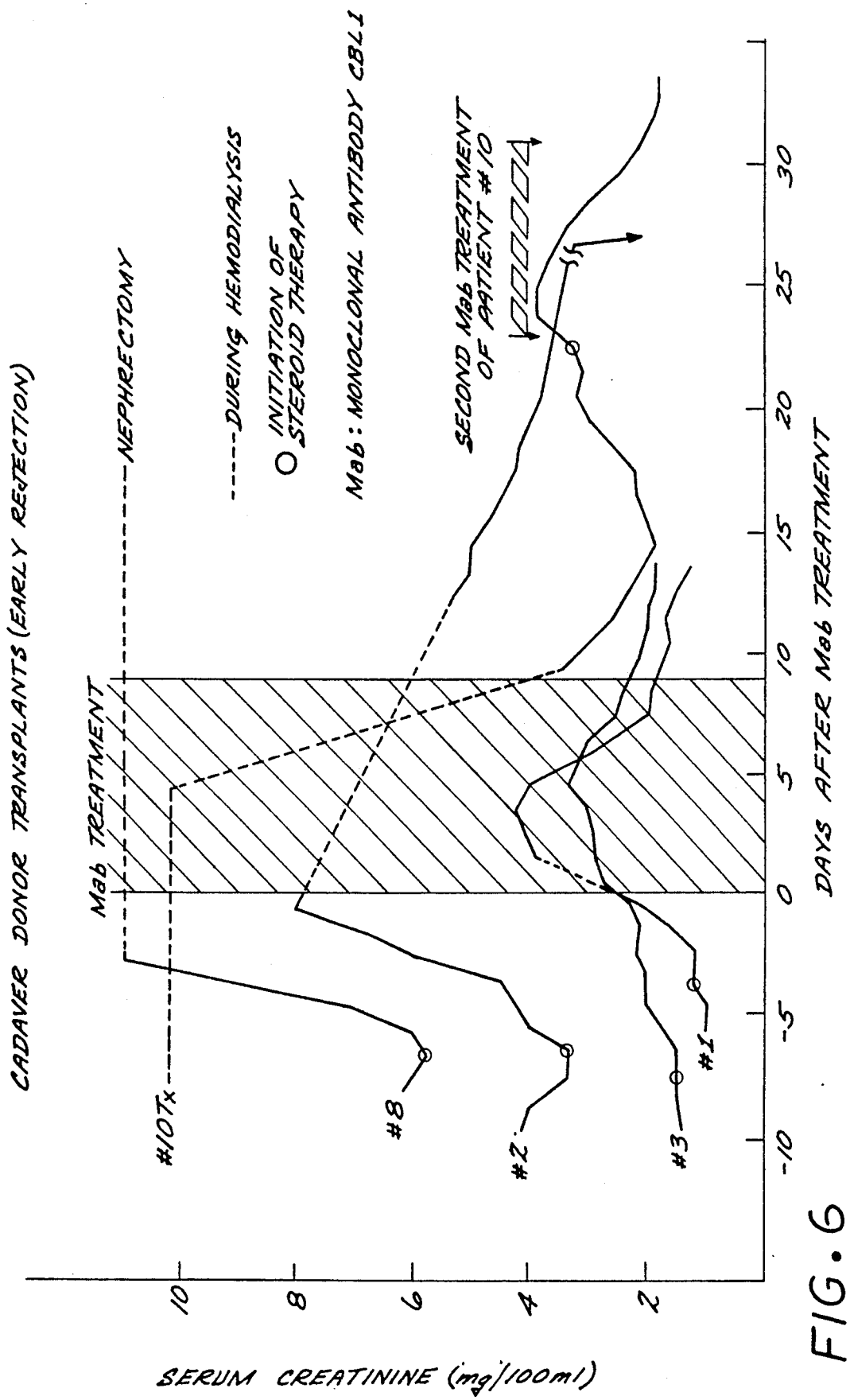
Figure 7:
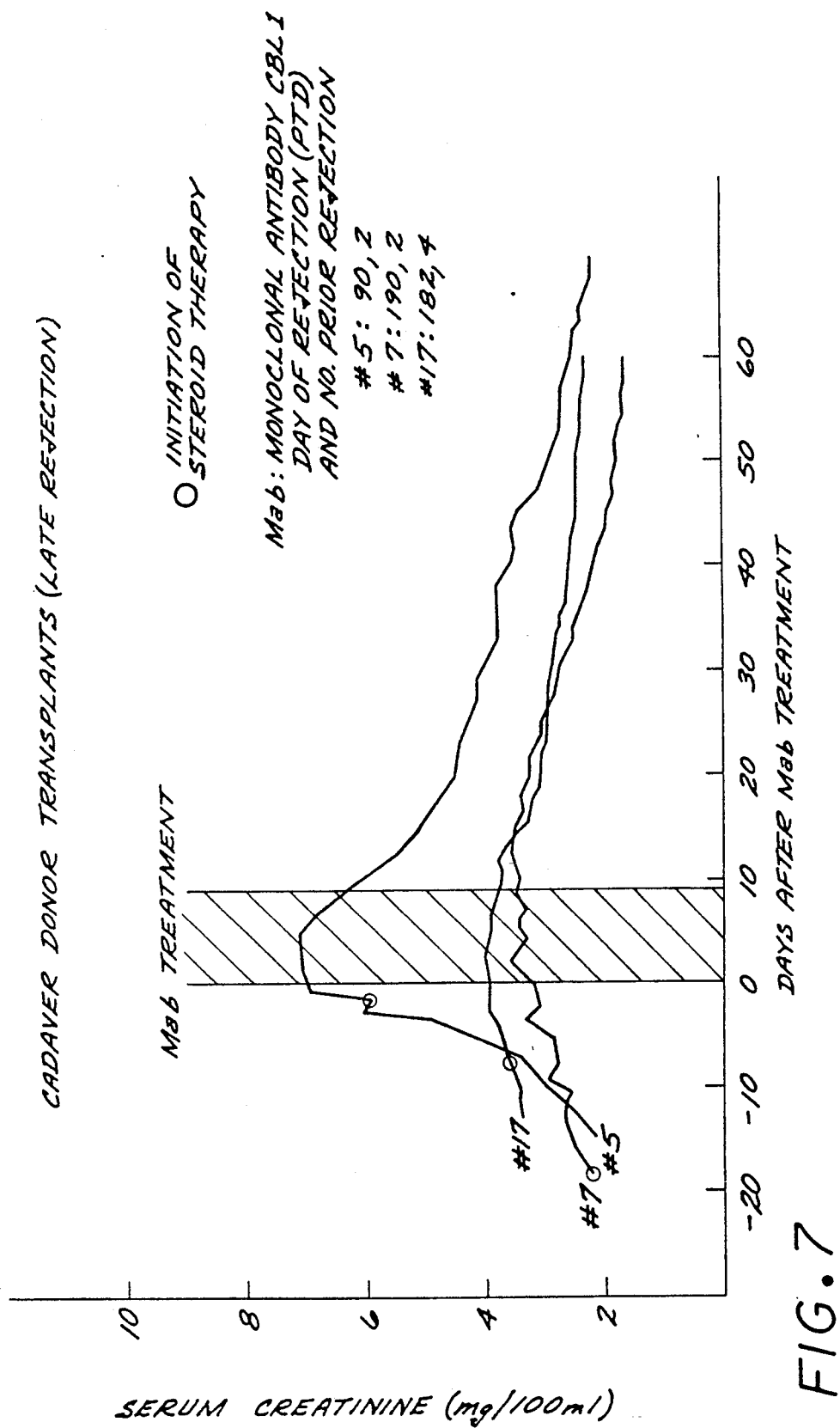
Figure 8:
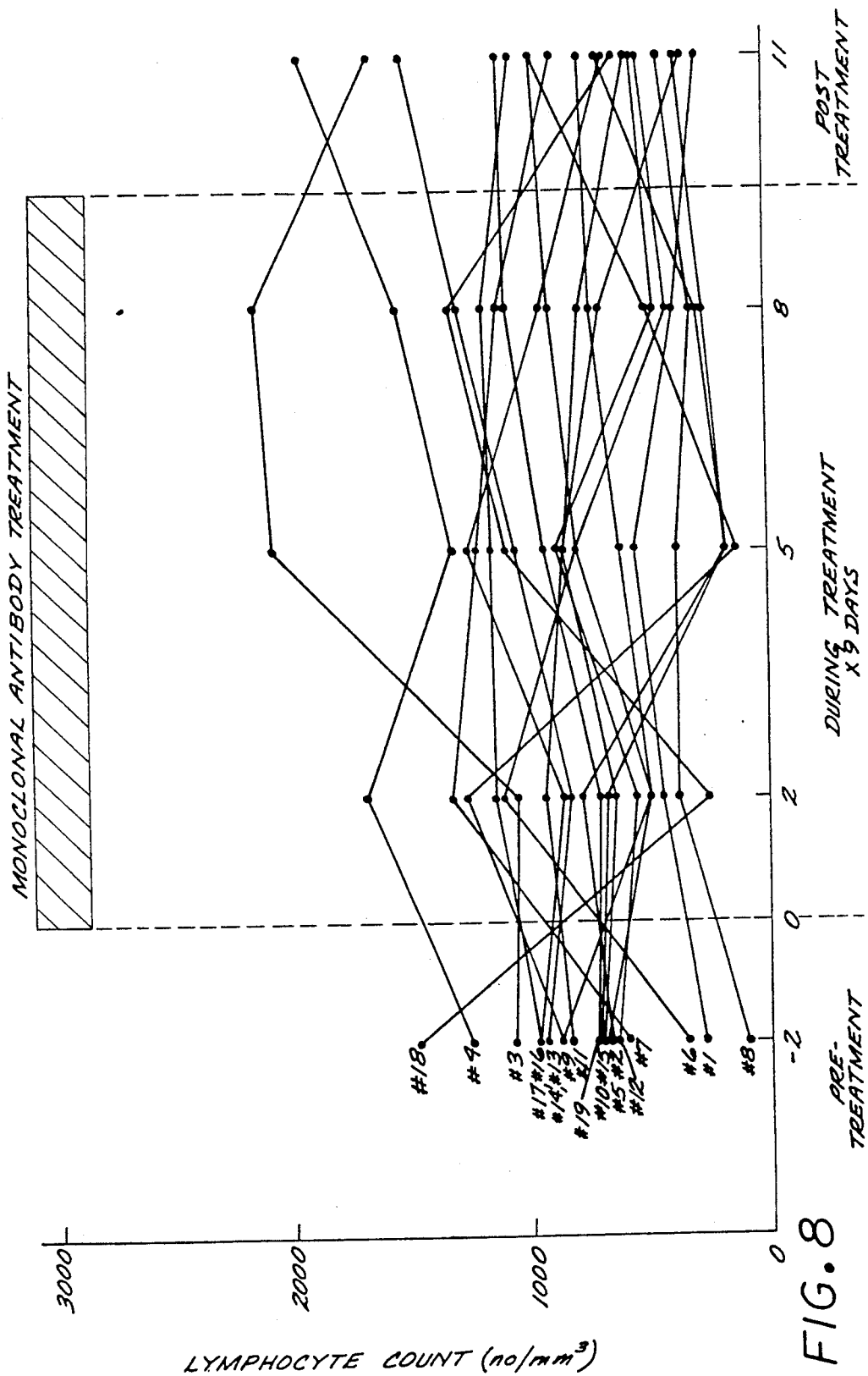
FIG. 8 shows the monitoring of blood lymphocyte counts during MA treatment.

Nineteen patients with severe steroid resistant kidney graft rejections were treated with the monoclonal antibody. Five mg in 200 ml of saline was given intravenously on 9 successive days. None of the 19 patients developed fever, vomiting, treatment created infections or other side effects. All patients had previously been immunosuppressed with conventional antirejection steroid drugs which had lowered blood counts and failed to reverse transplant rejection. There was a dramatic reversal of graft rejection in 17 cases. The creatinine clearance which was dangerously high indicating kidney rejection (greater than 4 mg/dL) showed a rapid decrease to normal levels starting on day 6 following treatment, (FIGS. 5-7). With MA treatment there was no fall in peripheral blood lymphocytes (FIG. 8), thrombocytopenia, and no reduction in peripheral blood monocyte count. Recurrence of graft rejection was uncommon after treatment. One patient (#10, FIG. 6) who had a recurrence of graft rejection 8 months after received a 2nd treatment that again reversed rejection. Apart from this case the majority of the treated patients have had functioning kidneys for more than 6 years. No other antibody or medication described in prior art has been able to reverse acute rejection with comparable long term success, lack of side effects and short duration of therapy.

A similar clinical study was done on three kidney transplant patients and six corneal graft patients. Conventional steroid rejection therapy had failed. Following i.v. MA-antigen complex treatment reversal of graft rejection was seen in all cases without side effects. The dose of MA-antigen complex ranged from 1.0 to 5.0 mg daily for 9 days in 100-200 ml of saline administered intravenously. The titer was 1:$10^4$ to 1:$10^5$. Blood counts and vital signs showed no adverse effects during or after treatment. In the case of the corneal graft rejection the patient's vision was very limited due to opaqueness caused by rejection. Following MA therapy normal vision was restored in all cases.

Six patients with advanced metastatic cancer have been treated with MA-antigen complex ranging from 1-20 mg over various periods of time depending on extent of disease. Tumor size was reduced following the treatment and no adverse side effects were noted. These studies are in their preliminary stages.

Figure 9:
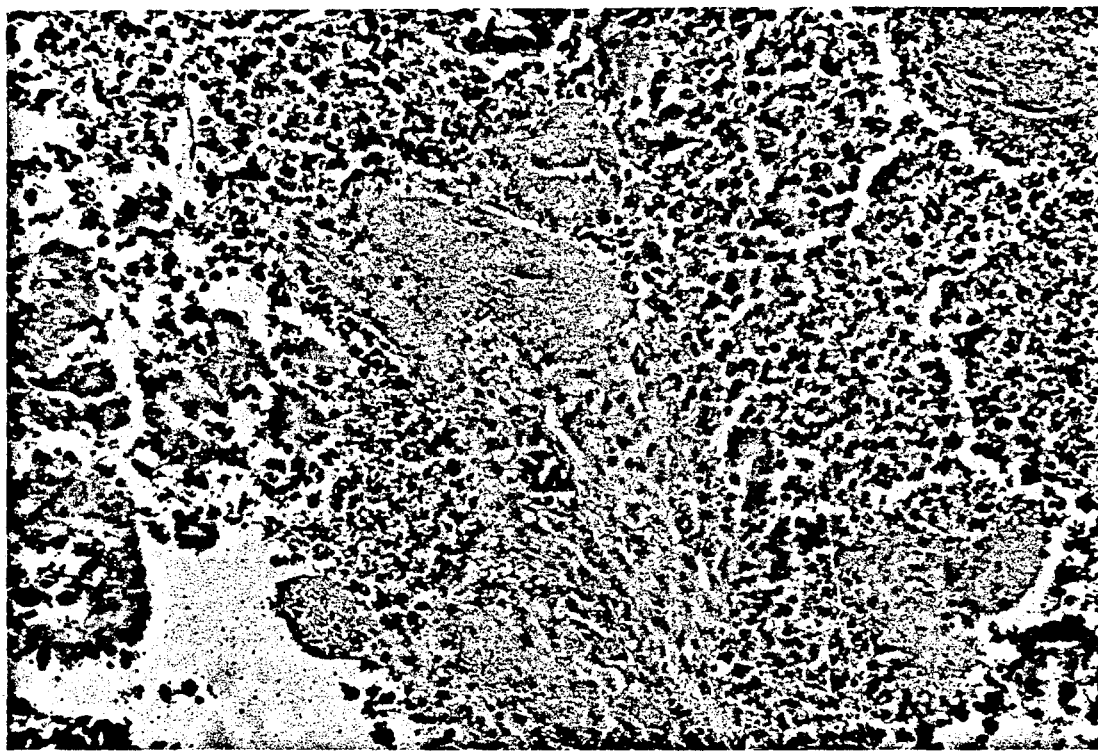
FIG. 9 shows a stained skin section containing areas of necrotic tissue. The patient (EC) was treated with MA complex.

Case 1. A 66 year old male (EC) with metastatic colon cancer in the lymph nodes, spleen, abdomen and liver 3 years following surgery had developed an ulcer following extensive chemotherapy and was hospitalized for intravenous feeding. Following intravenously 5 mg MA-antigen complex daily for 10 days a large palpable abdominal tumor became necrotic and the skin lesion healed. Several weeks later he died of malnutrition while still on intravenous feeding. Tissue sections taken from autopsy tissue showed extensive necrosis of tumor cells but no visible damage to normal tissue. FIG. 9 shows necrosis of malignant skin.

Case 2. A 48 year old male (GL) with a 2 cm diameter squamous cell carcinoma in the nasopharyngeal area received six 2.5 mg doses of MA-antigen complex intramuscularly. One week following the treatment the tumor was no longer visible by endoscopy. Four weeks later a scan by magnetic resonance imaging revealed no evidence of the tumor in the nasopharynx. No evidence of side effects were observed.

Case 3. A male (JB) with colorectal cancer with metastasis to the lymph nodes and lower abdomen causing large abscess on the left groin and protruding rectal tumor was treated with MA-antigen complex. Following ten daily treatments of 20 mg per day the tumor abscess healed completely and the protruding rectal tumor receded.

Case 4. A 58 year old male (JR) diagnosed as primary Dukes C colon cancer had lymph node and liver metastasis following surgical removal of the tumor in the colon. His CEA level following surgery was 16 mg/ml which indicated a poor prognosis. Following 5 months of chemotherapy his condition had not changed. 22 months following i.m. MA-antigeni complex treatment the lymph node metastasis receded and he is still alive and well with a single metastatic tumor in the liver.

Case 5. A 76 year old male (JB) had undergone surgery and readiation treatment for pancreatic cancer. Multiple netastasis remained and the prognosis was poor. CT scans show the complete regression of a 4 cm. tumor over a period of 3 months. The patient was treated over a period of 2 months with MA He is currently healthy and tumor free 20 months following treatment. Pancreatic cancer is fatal for 90% of patients within a period of one year.

Case 6. A 54 year old male (GB) diagnosed with squamous cell carcinoma of the lung showing 3½ cm mass in upper lobe received 8 treatments of MA complex. One month later, surgery on the lung revealed extensive necrosis of tumor. He is presently free of disease and in good health 2 years following treatment.

Patients treated with the MA-antigen reagent show human antibodies against the growth factor. This evidence indicates that a mechanism of active immunotherapy is involved.

The antigen is isolated from NP40 lysates of lymphoid cells and purified by G50$^R$ gel filtration. Fractions that had a molecular weight of 15K dalton stimulated the growth of tumor cells in culture as in Table 3. They also showed immunodiffusion precipitin lines with the monoclonal antibody and antigen induced human serum antibodies from treated patients. Human growth factor and mouse growth factor both give contiguous precipitin lines of identity. Other G50 fractions did not stimulate cell growth or show precipitin lines.

G. Detection of two identical antigenic epitopes.

The unique structural feature of the antigenic Growth Factor is the presence of two identical but separated epitopes. When purified antigen was added to washed tumor cells in PBS on a glass slide or in a test tube the cells rapidly formed large aggregates. Antibody coated latex beads strongly aggregated or agglutinated in the presence of growth factor from both mouse and human cells. Excess antigen will prevent agglutination by saturating all the receptor sites. Cells and beads are cross linked by the two antigenic epitopes binding to receptors on two different cells or beads. (See FIG. 10 for mechanisms of agglutination.)

Monoclonal antibodies do not usually form precipitin lines in agarose immunodiffusion because they bind to only a single antigenic site. In this case the MA will form precipitin lines with the growth factor antigen because it expresses two identical epitopes per molecule that will cross link several MA molecules to form a lattice structure. By gel filtration in low pH buffer the MA can be separated from its antigen.

Uses

Immunization of vertebrates against a challenge of tumor cells.

Balb/c mice preimmunized with purified human growth factor antigen could withstand a subcutaneous challenge of Balb/c hybridoma cells. Because mouse growth factor antigen can produce active immunization in patients it should be able to protect humans from cancer by immunization in the same way human growth factor antigen does in mice.

The mouse antigenic growth factor stimulates the production of lymphocytes in mice. Therefore human growth factor antigen may stimulate the level of circulating lymphocytes.

A further use of the invention is a test for cancer by detecting the amount of antigen in the serum or urine excreted by malignant cells. The free monoclonal antibody is immobilized to a convenient matrix (latex beads, nitrocellulose paper etc.). The immobilised MA is incubated first with the unknown antigen source, then with labeled antigen. The dilution of the unknown that will block the binding of the labeled antigen is proportional to the concentration of antigen.

Immunodiagnostic methods in for the form of kits can assay for the presence of the protein growth factor in human cells and fluids. These kits containing several components one of which is said monoclonal antibody or heteroantisera complex with antigen which is incubated with the specimen. Following incubating the above antibodies with a specimen, the specimens are washed free of excess antibody. The bound antibody is then detected by a second component of the kit containing a means for detecting the formation of an immune complex. A more rapid method is achieved by said antibody or antigen bound to a detectable label such as a florescent label, peroxidase enzyme or radioactive label that is observed bound to target cells following one incubation and washing. Soluble antigen in fluids is detected by incubating fluid with predetermined amount of labeled antibody and observing the inhibition of binding of the labeled antibody compared to control to tumor cells, lymphoblastoid cells or antigen immobilized on polymer beads or solid supports such as nitrocellulose paper. This method can also detect said antibodies in body fluids by observing binding of labeled antibody to antigen bound to tumor cells, lymphoblastoid cells or immobilized supports.

Said antigen can be detected in a soluble form in cell lysates or biological fluids by binding to said monoclonal and heteroantibodies in opposite wells of agarose immunodiffusion plates where precipitin lines show antigen-antibody complexes. Both said monoclonal antibody and heteroantibodies to antigen will show precipitin lines.

The invention is potentially useful in the treatment of all autoimmune diseases and graft versus host disease by removing the activated lymphocytes that are causing the disease. Patients with these diseases have been found to have high percentages of circulating activated lymphocytes. The invention is also useful for treating patients with AIDS. The treatment destroys activated helper T lymphocytes that contain the AIDS virus (HIV).

What is claimed is:

1. A partially purified antigen of vertebrate source that has the following properties:
    (a) it functions as an autocrine growth factor produced by tumor cells and activated lymphocytes,
    (b) it binds to the surface membrane of tumor cells and stimulates the growth of these cells and cells of the lymphoid series,
    (c) it is present on the cell membrane and within the cytoplasm of tumor cells and activated lymphocytes,
    (d) it is present in the cytoplasm of unstimulated normal peripheral blood lymphocytes but when these cells are stimulated by antigens or by mitogens, said antigen appears also on the cell membrane,
    (e) it is present on lymphocytes activated in vitro by mitogens,
    (f) it is present in the medium from growing cancer cells and in the serum of patients with cancer and diseases in which activated lymphocytes are present,
    (g) its molecular weight is approximately 15,000 daltons,
    (h) is capable of binding to CBL1 monoclonal antibody which is produced by the hybridoma cell line having the ATCC number HB8214.

2. A partially purified protein or polypeptide of natural or biosynthetic sources having antigenic determinants identical to determinants of the antigen of claim 1, said protein or polypeptide bound to a detectable label or insoluble phase.

3. A method for assaying a biological specimen for the presence of antibodies to the antigen of claim 1 or for its cell receptor on cells or in body fluids, comprising the steps of incubating said specimen with labeled or unlabeled antigen of claim 1 or 2, and determining whether or not an immune complex or antigen-receptor complex is formed.

* * * * *